United States Patent [19]
Johnston et al.

[11] 4,393,688
[45] Jul. 19, 1983

[54] PIEZOELECTRIC KNOCK SENSOR

[75] Inventors: Daniel U. Johnston; George A. Shinkle, both of Anderson, Ind.

[73] Assignee: General Motors Corporation, Detroit, Mich.

[21] Appl. No.: 322,989

[22] Filed: Nov. 19, 1981

[51] Int. Cl.³ ............................................. G01L 23/22
[52] U.S. Cl. ........................................... 73/35; 73/654; 310/329
[58] Field of Search ................... 73/35, 654, 658, 660; 310/319, 328, 329, 355

[56] References Cited

U.S. PATENT DOCUMENTS

| 3,042,744 | 7/1962 | Shoor | 310/329 |
| 3,891,869 | 6/1975 | Scarpa | 310/334 |
| 4,254,354 | 3/1981 | Keem | 73/35 X |

*Primary Examiner*—James J. Gill
*Attorney, Agent, or Firm*—Robert M. Sigler

[57] ABSTRACT

A piezoelectric knock sensor has a case comprising a mounting stud, flexing plate and cover. The flexing plate has a surface provided with a plurality of raised radial ridges. A piezoelectric disk is affixed to the surface with an adhesive and abuts the ridges for improved strain transmission and reliable electrical ground contact. A spring contact further biases the disk against the ridges during assembly bonding of the adhesive; and excess adhesive can flow radially outward between the ridges.

2 Claims, 4 Drawing Figures

PIEZOELECTRIC KNOCK SENSOR

BACKGROUND OF THE INVENTION

This invention relates to piezoelectric knock sensors adapted for mounting on an internal combustion engine and particularly an interactive piezoelectric knock sensor of the type shown in U.S. Pat. No. 4,254,354 issued to John E. Keem. The knock sensor of this invention is an improvement over that shown in the above-identified U.S. patent in the mounting and electrical connection of its piezoelectric element to the flexing plate comprising the bottom of the case.

In an interactive piezoelectric knock sensor of the type contemplated, a flat piezoelectric disk is attached to a flexing plate which comprises the bottom of a sensor case having a rigid mounting stud affixed thereto. With the mounting stud attached to an internal combustion engine, the flexing plate serves as a spring between the mass of the remainder of the sensor case and the engine itself, which vibrate in response to engine knock induced vibrations interactively in a plurality of axial and transverse modes of vibration for a broader resonance frequency characteristic than is possible in the standard isolated resonance piezoelectric knock sensor. The piezoelectric disk, being attached to the flexing plate over a substantial portion of the flexing area thereof, partakes of these vibrations and generates electrical output signals in response thereto between its opposite faces. One face of the piezoelectric element is electrically connected to an output signal terminal while the other face must be reliably grounded to the flexing plate of the sensor case. In addition, the piezoelectric disk must be reliably affixed to the surface of the flexing plate so that it will indeed partake of the full range of vibrations thereof.

In the above-identified U.S. Pat. No. 4,254,354 it is disclosed that the piezoelectric element or disk may be affixed to the flexible plate with an epoxy material between the surfaces thereof and that, if the epoxy is not electrically conductive, electrical ground contact may be established by conducting elements pressed therebetween or by alternating projections and valleys in the surface of the flexing plate, the projections of which may contact the piezoelectric disk while the valleys are filled with the epoxy material. Both of these methods have been tried and found to be satisfactory for single samples of the sensor.

For mass production of the sensor in large quantities, however, it is desirable to provide a method of establishing the ground connection between the piezoelectric disk and the flexing plate which simplifies the assembly process by minimizing the number of parts involved and separate operations required and coordinates well with other steps in the assembly process.

SUMMARY OF THE INVENTION

Therefore, it is an object of this invention to provide a piezoelectric knock sensor of the type having a piezoelectric element affixed to a flexing plate for flexure with the vibrations thereof and means providing a reliable and easily, inexpensively manufacturable ground connection therebetween.

This object and others are obtained in a piezoelectric knock sensor comprising a flexing plate supported on a mounting element and having a surface comprising a plurality of raised radial ridges, a piezoelectric disk affixed to the surface of the plate in contact with said ridges with an adhesive substance between said ridges, a cover affixed to the periphery of the plate and including an electric output terminal and spring means compressed between the cover and the piezoelectric element biasing the same against the ridges and establishing electrical contact between the piezoelectric element and output terminal.

The radial ridges promote improved strain transmission to the piezoelectric element from the flexing surface through the long areas of contact therebetween and allow epoxy or adhesive flow radially outward from under the piezoelectric element during assembly and bonding of the piezoelectric element to the flexing plate. In addition, the long, sharp, raised ridges promote improved electrical contact with the additional benefit that sufficient pressure may be obtained for reliable bonding during sensor assembly from the spring contact alone. Further details and advantages will be apparent from the accompanying drawings and following description of a preferred embodiment.

DESCRIPTION OF THE PREFERRED EMBODIMENT

Figure 1:
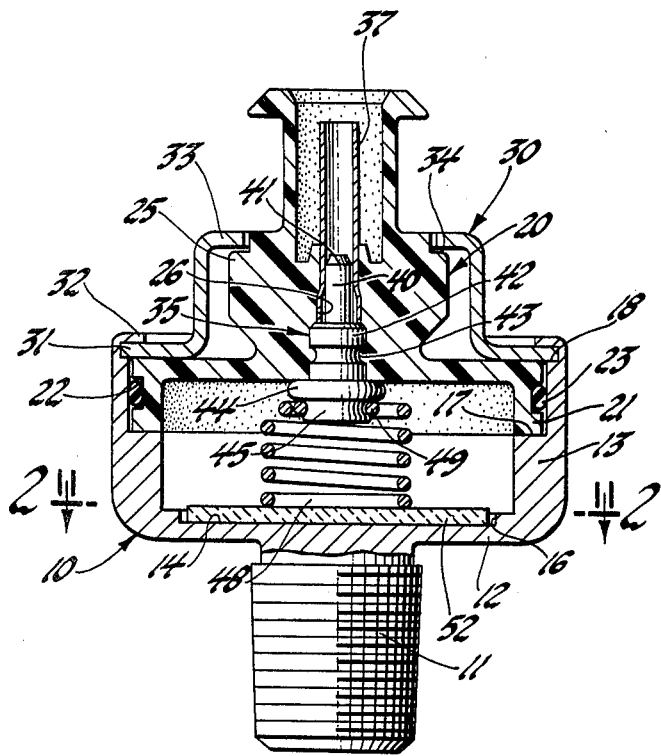
FIG. 1 is a partial axial sectional view of a knock sensor according to this invention.
Figure 4:
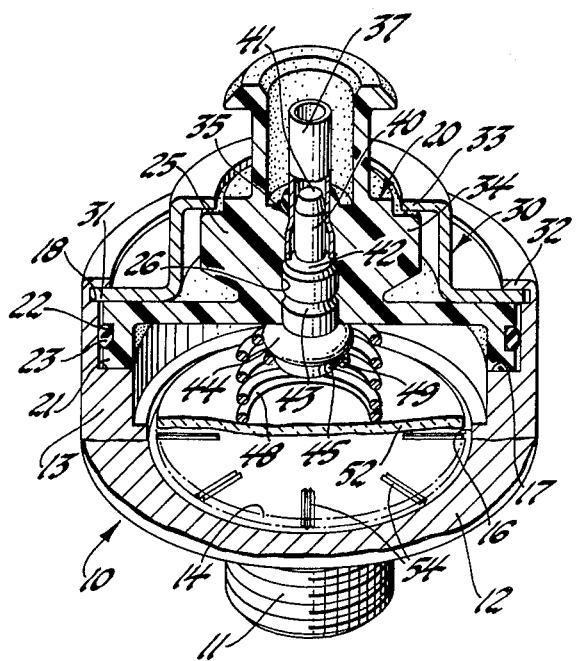
FIG. 4 is a partially cutaway oblique view of the sensor shown in FIG. 1.

Referring to FIGS. 1 and 4, the sensor according to the invention includes a housing member 10 comprising a rigid mounting stud 11, a flexing plate 12 and a cylindrical wall 13. Mounting stud 11 projects axially from the center of flexing plate 12 and is threaded in a standard thread pattern for rigid mounting on a component of an internal combustion engine. Flexing plate 12 includes, on its inner surface 14 opposite mounting stud 11, a shallow depression defined by circular shoulder 16, which aids in the location of the piezoelectric element during assembly of the sensor. Cylindrical wall 13 is a comparatively rigid cylinder which projects from the periphery of flexing plate 12 in a direction opposite that of mounting stud 11. Cylindrical wall 13 has a first reduction in wall thickness at a shoulder 17 and a second reduction in wall thickness at a shoulder 18. Housing member 10 is made of steel and inner surface 14 is zinc plated for adhesive bonding suitability.

An insulator 20 has a lower peripheral rim 21 which abuts shoulder 17 in cylindrical wall 13 of housing member 10. Just above lower peripheral rim 21, an outer cylindrical groove 22 in insulator 20 contains a sealing O-ring 23 compressed between insulator 20 and cylindrical wall 13 of housing member 10. Insulator 20 further includes an upper portion 25 having an axially central opening 26 adapted to receive a terminal assembly. Insulator 20 is formed from a 30% glass filled polyester material such as Velox 420 or its equivalent.

A cover 30 has a lower peripheral edge 31 which abuts shoulder 18 in cylindrical wall 13 of housing member 10 and is retained by the crimped-over upper end 32 of cylindrical wall 13. Cover 30 is stamped from steel and zinc plated. The upper or inner peripheral edge 33 of cover 30 abuts a shoulder 34 in insulator 20.

A terminal assembly 35 includes a terminal 37, a post 40 and a spring 48. Post 40 includes an upper cylindrical stud 41 over which is pressed the tubular terminal 37 to a shoulder 42. Post 40 further comprises a circumferential groove 43 between shoulder 42 and another shoulder 44 and a spring mounting stud 45 beyond shoulder 44. Post 40 is made of tin plated steel. Spring 48 is a coil spring made of tin plated music wire with a reduced diameter top coil 49 which surrounds and is staked to spring mounting stud 45 adjacent shoulder 44. Terminal assembly 35 is pressed into axially central opening 26 of insulator 20 up to shoulder 44 of post 40 ultrasonically so that some of the material of insulator 20 flows into groove 43 of post 40 for retention thereof. Thus, in the assembled sensor, terminal 37 projects outward from insulator 20 for outside connection and spring 48 extends toward inner surface 14 of flexing plate 12.

A piezoelectric disk 52 having silver electrodes on its opposite flat faces is disposed against inner surface 14 of flexing plate 12 and bonded thereto for flexure therewith by an epoxy adhesive material. Spring 48 is compressed between shoulder 44 of post 40 and one surface of piezoelectric disk 52 so that an electrical conduction path is formed between that surface of piezoelectric disk 52 and terminal 37 through spring 48 and post 40.

Figure 3:
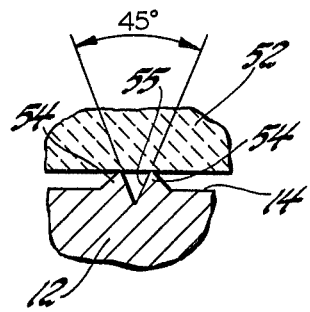
FIG. 3 is a partial section view along lines 3—3 in FIG. 2.
Figure 2:
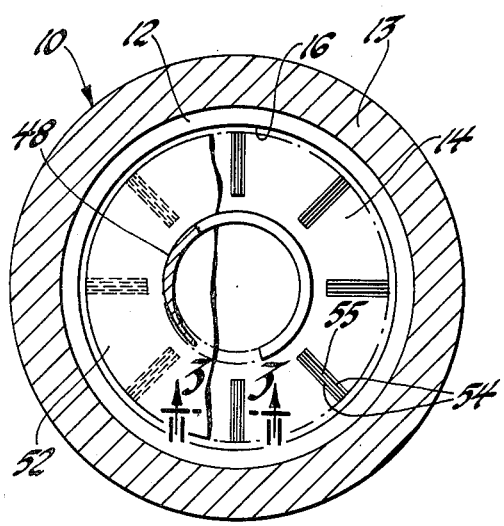
FIG. 2 is a section view along lines 2—2 of FIG. 1.

The opposite surface of piezoelectric disk, that adjacent inner surface 14, is provided with a ground connection through housing member 10 and the engine ground system by a series of radial, raised ridges 54 in inner surface 14. These ridges are formed by stamping a series of radial grooves 55 in inner surface 14, the ridges being formed on either side of each groove by the displaced material, as shown in FIG. 3. The height of the ridges above inner surface 14 is controlled by the tooling and the force applied during the stamping operation. In this preferred embodiment, a series of eight 45° grooves are provided at regular angular intervals around inner surface 14 so that eight pairs or a total of 16 radial ridges are provided. The ridges are long enough and sufficiently numerous to provide reliable electrical contact between inner surface 14 of flexing plate 12 and piezoelectric disk 52 as well as improved mechanical strain transmission therebetween during flexing caused by engine vibrations. The electrical contact provided is so good that, during the assembly process, the force of spring 48 alone is sufficient to hold the piezoelectric disk against the ridges 54 during the epoxy bonding operation. Finally, the radial arrangement of ridges 54 and grooves 55 allow radial outward flow of epoxy during original placement of the piezoelectric disk 52 so that this epoxy will not become trapped under piezoelectric disk 52 and thus prevent reliable electric ground contact.

The preceding preferred embodiment is not the only embodiment of this invention that will occur to those skilled in the art. Therefore, this invention should be limited only by the claims which follow.

The embodiments of the invention in which an exclusive property or privilege is claimed are defined as follows:

1. A knock sensor for an internal combustion engine comprising, in combination:
   a mounting element adapted for rigid attachment to the engine;
   a flexing plate supported on the mounting element and adapted to execute plate vibrations in response to knock events in the engine, the plate having a surface comprising a plurality of raised radial ridges;
   a piezoelectric disk affixed to the surface of the plate for flexure with vibrations thereof in abutment with the radial ridges by means of an adhesive substance between the raised radial ridges, said ridges providing internal electrical ground contact for one surface of the piezoelectric disk through the plate, mounting element and engine, as well as strain transmission between the plate and the disk;
   a cover affixed to the periphery of the plate, the cover including an electric output terminal; and
   spring means compressed between the cover and the other surface of the piezoelectric disk, said spring means being in electrical contact with the electric output terminal, the radial arrangement of said ridges permitting radial outflow of excess adhesive to permit the spring means to force the piezoelectric element into contact with said ridges, whereby good internal electrical ground contact in the sensor is assured.

2. A knock sensor for an internal combustion engine comprising, in combination:
   a mounting element adapted for rigid attachment to the engine;
   a flexing plate supported on the mounting element and adapted to execute plate vibrations in response to knock events in the engine, the plate having a surface comprising a plurality of radial grooves with a raised radial ridge on each side thereof;
   a piezoelectric disk affixed to the surface of the plate for flexure with vibrations thereof in abutment with the radial ridges by means of an adhesive substance between the raised radial ridges, said ridges providing internal electrical ground contact for one surface of the piezoelectric disk through the plate, mounting element and engine as well as strain transmission between the plate and the disk;
   a cover affixed to the periphery of the plate, the cover including an electrical output terminal; and
   spring means compressed between the cover and the other surface of the piezoelectric disk, said spring means being in electrical contact with the electric output terminal, the radial arrangement of said ridges permitting radial outflow of excess adhesive to permit the spring means to force the piezoelectric element into contact with said ridges, whereby good internal electrical ground contact in the sensor is assured.

* * * * *